(12) United States Patent
Lu et al.

(10) Patent No.: US 8,138,214 B2
(45) Date of Patent: *Mar. 20, 2012

(54) PHARMACEUTICAL COMPOSITION

(75) Inventors: Yaoru Lu, Shanghai (CN); Jianhui Guo, Shanghai (CN)

(73) Assignee: Shanghai Allist Pharmaceutical, Inc., Shanghai (CN)

( * ) Notice: Subject to any disclaimer, the term of this patent is extended or adjusted under 35 U.S.C. 154(b) by 60 days.

This patent is subject to a terminal disclaimer.

(21) Appl. No.: 12/497,282

(22) Filed: Jul. 2, 2009

(65) Prior Publication Data

US 2009/0326025 A1 Dec. 31, 2009

Related U.S. Application Data

(63) Continuation of application No. PCT/CN2008/000048, filed on Jan. 7, 2008.

(30) Foreign Application Priority Data

Jan. 5, 2007 (CN) .......................... 2007 1 0036237

(51) Int. Cl.
*A01N 43/64* (2006.01)
*A61K 31/41* (2006.01)
*C07D 257/00* (2006.01)

(52) U.S. Cl. ....................... 514/381; 548/253
(58) Field of Classification Search .......... 514/381
See application file for complete search history.

(56) References Cited

U.S. PATENT DOCUMENTS

| 5,196,444 | A | | 3/1993 | Naka et al. |
| 5,298,519 | A | * | 3/1994 | Binder et al. ............ 514/381 |
| 5,616,599 | A | | 4/1997 | Yanagisawa et al. |
| 5,990,134 | A | * | 11/1999 | Alam ........................ 514/338 |
| 2009/0036505 | A1 | | 2/2009 | Guo et al. |

FOREIGN PATENT DOCUMENTS

| CN | 1071426 | 4/1993 |
| EP | 0 253 310 | 1/1988 |
| WO | 2005/011646 | 2/2005 |
| WO | WO 2007/095789 | 8/2007 |

OTHER PUBLICATIONS

Yanagisawa, Nonpeptide Angiotensin II Receptor Antagonists: Synthesis, Biological Activities, and Structure—Activity Relationships of Imidazole-5-carboxylic Acids Bearing Alkyl, Alkenyl, and Hydroxyalkyl Substituents at the 4-Position and Their Related Compounds, J. Med. Chem., 1996, 39 (1), pp. 323-338.*

International Search Report issued in PCT/CN2008/000048, dated Apr. 17, 2008.

Naylor et al., "Potent imidazole angiotensin II antagonists: acyl sulfonamides and acyl sulfamides as tetrazole replacements," Bioorganic & Medicinal Chemistry Letters, vol. 4, No. 1, 1994, pp. 69-74.

* cited by examiner

*Primary Examiner* — Sreeni Padmanabhan
*Assistant Examiner* — Layla Soroush
(74) *Attorney, Agent, or Firm* — Hamre, Schumann, Mueller & Larson, P.C.

(57) ABSTRACT

The invention provides a new pharmaceutical compositions for treating cardiovascular disease, which contains the active component 2-butyl-4-chloro-1-[2'-(1H-tetrazol-5-yl)1,1'-biphenyl-methyl]imidazole-5-carboxylic acid, 1-[(isopropoxy)carbonyloxy]methyl ester dispersing in pharmaceutically acceptable carriers. The composition can be prepared to solid dosage forms e.g. powders, granules, dripping pills, micro-pellets, tablets, capsules, lozenges etc. by mouth or other way e.g. sublingual administration etc.

12 Claims, No Drawings

PHARMACEUTICAL COMPOSITION

CROSS-REFERENCE TO RELATED APPLICATIONS

This application is a continuation of International Patent Application No. PCT/CN2008/000048, filed on Jan. 7, 2008, which claims priority to Chinese Application No. 200710036237.5, filed on Jan. 5, 2007, the entire contents of both of which are incorporated herein by reference.

TECHNICAL FIELD

The invention relates to pharmaceutical compositions, more particularly to a pharmaceutical composition containing a new compound having pharmaceutical activities, to a method for the preparation of the composition, and to a use of the composition in the preparation of cardiovascular medicaments.

BACKGROUND OF THE INVENTION

Angiotensin II, a main vasoconstrictor hormone of renin-angiotension-aldosterone system (RAAS), plays an important role in pathological physiology of many chronic diseases. The production approach of Angiotensin II which is present in various tissues is mainly as follows: angiotensinogen acted on by renin can be converted to angiotensin I (Ang I) of decapeptide which only has little activity in contraction of blood vessel; and can be further converted by angiotensin converting enzyme to angiotensin II (Ang II) of octapeptide which is the final physiological active substance of renin-angiotension-aldosterone system (RAAS) and can induce physiological functions such as contraction of blood vessel and elevation of blood pressure by binding to specific angiotensin II (ATII) receptor.

EP0253310 discloses a series of imidazole derivatives. After researching, E. I. Du Pont de Nemours and Company (US) found that a compound of DUP753 had a good effect on lowering blood pressure. It was approved in 1994 and became the first non-peptide type Ang II receptor antagonist, i.e. losartan potassium, which inhibited contraction of blood vessel by selectively blocking the actions of angiotensin II of smooth muscle in blood vessel on its Ang I receptor to achieve the functions of dilating blood vessel and reducing blood pressure.

With the development and marketing of losartan potassium, various medical R&D organizations and companies began studies on structure of Ang II receptor antagonists in succession. U.S. Pat. No. 5,196,444 discloses a series of benzimidazole derivatives and processes for preparation thereof. Such derivatives have angiotensin II antagonistic activity and antihypertensive activity and thereby can be used to treat hypertensive diseases. Among them, candesartan was developed and marketed in 1997 by Takeda Chemical Industries, Ltd. (JP), which releases ester group in vivo and is hydrolyzed to its active metabolite to exert the action of lowering blood pressure.

U.S. Pat. No. 5,616,599 discloses a series of 1-biphenylmethylimidazole derivatives with structures similar to that of losartan. The significant difference in structures between them is that the chlorine atom at the 4-position of the imidazole ring of losartan is converted to 1-hydroxy-1-methylethyl, and the 5-position of that is converted to a carboxyl group, hydroxyl group or pro-drug structures such as ester or amide. It is demonstrated to have good activity in reducing blood pressure. Therefore, Sankyo Company, Ltd. (JP) developed and marketed a drug of olmesartan.

CONTENTS OF INVENTION

The present invention provides a pharmaceutical composition containing an active pharmaceutical ingredient, in particularly a compositions containing a new Ang II receptor antagonists. The composition could be in the form of powders, granules, dripping pills, micro-pills, tablets, capsules, lozenges or other proper solid preparations. Alternatively, the composition could the solid preparations dispersed by liquid before being administered. This novel pharmaceutical composition can be used for treating cardiovascular diseases.

A further purpose of the present invention is to provide a composition for the solubilization of said active ingredient, in which said active ingredient is highly dispersed into carrier materials, especially a kind of water-soluble carrier material, so as to increase the dissolution rate of the active ingredient, and to improve the bioavailability thereof.

Another purpose of the present invention is to provide an oral solid dosage form prepared from the solubilizing compositions comprising said active ingredient. Said solid dosage forms could be in the form of powders, granules, dripping pills, micro-pills, tablets, capsules, lozenges and other proper ones. In one embodiment, the solid dosage form is dispersed by liquid before being swallowed. The present invention also provides a method for preparing the composition.

The other purpose of the present invention is to provide a novel pharmaceutical composition useful in treating cardiovascular diseases.

A further purpose of the present invention is to provide a method of treating cardiovascular diseases in human being, in particular a method for treating hypertension.

Another purpose of the present invention is to provide a technical solution to increase the gastrointestinal absorption of the medicament.

The present applicant described a series of imidazole-5-carboxylic acid derivatives in a PCT application (PCT/CN2006/001914). Their structural character relies on the structure of geminate diacid esters at the 5-position of the imidazole ring. This type of compounds show significantly antihypertensive activity. Compared with other Ang II receptor antagonist, this type of imidazole-5-carboxylic acid derivatives have the advantage of lower toxicity. The following compounds are more particularly disclosed in this PCT application:

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, shown as formula I.

Formula I

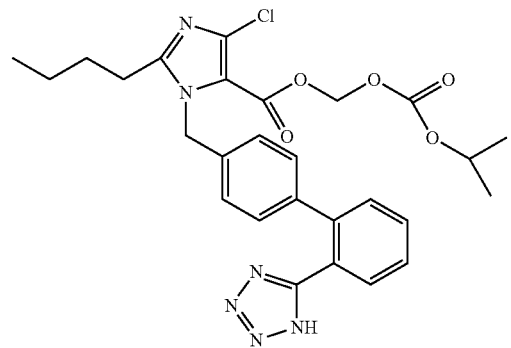

This active agent can be administered to the patients in a conventionally oral dosage form. In the oral dosage form, the solubility of the active agent is closely related with the bioavailability of the medicaments in the body. Methods for improving the solubility could be comminuted, such as mechanical comminution, micronization and so on, which reduces volumes of granules, and increases the surfaces of granules for improving the solubility of the active agent. Furthermore, the structure of the compound could be changed, for example, to form the salts or esters thereof. Moreover, the means of preparing dosage forms, such as clathration by cyclodextrin, solid dispersing, adding solubilizing agents and so on, could be used.

The present invention has studied the pharmaceutical composition containing compound with formula I: 2-butyl-4-chloro-1-[2'-(1H-tetrazol-5-yl) 1,1'-biphenyl-methyl]imidazole-5-carboxylic acid, 1-[(isopropoxycarbonyl)oxy]methyl ester as active agent extensively and deeply, and to develop proper formulations for clinic application.

As used herein, "active agent" or "pharmacologically active ingredient" represents compound I: 2-butyl-4-chloro-1-[2'-(1H-tetrazol-5-yl) 1,1'-biphenyl-methyl]imidazole-5-carboxylic acid, 1-[(isopropoxycarbonyl)oxy]methyl ester.

Oral Solid Composition

The present invention firstly provides a solid composition containing 2-butyl-4-chloro-1-[2'-(1H-tetrazol-5-yl) 1,1'-biphenyl-methyl]imidazole-5-carboxylic acid, 1-[(isopropoxycarbonyl)oxy]methyl ester, prepared by adding pharmaceutically acceptable carrier materials (also called excipients).

One aspect of the present invention is to provide oral solid dosage forms. Carrier materials in the composition are selected from the group consisting of fillers, disintegrants, wetting agents, binders, surfactants, lubricants, glidants, correctants, colorants and other types of excipient for solid dosage forms. The composition may be, but are not limited to, in the form of powders, granules, micro-pellets, capsules, tablets or lozenges. It is known in this art that tablets could be plain tablets, film coated tablets, sugarcoating tablets, bilayer or multi-layer tablets, effervescent tablet, dispersible tablet, oral disintegration tablets, sustained releasing tablets. Even though the compositions are conventionally suitable for oral administration, they can also be chosen for other administration methods, such as sublingual administration, or dosage forms dispersed by liquid before being swallowed.

The fillers are selected from at least one of the following components: calcium carbonate, magnesium carbonate, calcium phosphate, calcium sulfate, magnesium oxide, calcium carboxymethylcellulose, sodium carboxymethylcellulose, sucrose, lactose, fructose, xylitol, starch or the derivates thereof, dextrin, microcrystalline cellulose, or the mixture thereof.

The disintegrants are selected from at least one of the following components: starch, alginic acid, calcium carboxymethylcellulose, sodium carboxymethylcellulose, croscarmellose sodium, crospolyvinylpyrrolidone, low-substituted hydroxypropyl cellulose, microcrystalline cellulose, methyl cellulose, or the mixture thereof.

The surfactants are selected from at least one of the following components: sodium dodecylsulfate, poloxamer, tweens, bromide hexadecane trimethylamine, Sodium Laurylsulfate, sodium stearyl alcohol sulfonate, polyoxyethylene high-grade fatty alcohol, sucrose esters, sorbitol fatty ester, soybean phospholipid, or the mixture thereof.

The wetting agents are selected from at least one of the following components: distilled water, ethanol, starch paste, or the mixture thereof.

The binders are selected from at least one of the following components: acacia, gelatin, tragacanth, dextrin, polyvinylpyrrolidone, starch or its derivates, algin, sorbitol, syrup, hypromellose, methyl cellulose, hydroxypropyl cellulose, hydroxyethylcellulose, ethylcellulose, sodium carboxymethylcellulose, calcium carboxymethylcellulose, glucose, polymethacrylate, or the mixture thereof.

The lubricants are selected from at least one of the following components: calcium stearate, glyceryl monostearate, glyceryl palm stearate, magnesium stearate, microcrystalline cellulose, sodium benzoate, sodium chloride, sodium dodecylsulfate, sodium stearine fumarate, talc powder, zinc stearate, polyethylene glycol, or the mixture thereof.

The glidants are selected from at least one of the following components: colloidal silicon dioxide, powdered cellulose, magnesium trisilicate, silicon dioxide and talc powder, or the mixture thereof.

The correctants are selected from the following components: aspartame, stevioside, fructose, glucose, syrup, honey, xylitol, mannitol, lactose, sorbitol, maltol, glycyrrhizic acid, phyllodulcin, essences, ethereal oils; the colorants are selected from natural or artificial pigments.

It is easy for a person skilled in this art to understand that, for oral solid dosage forms, the above exemplified substances do not intend to limit the technical solution in the present application. Those unlisted substances which are conventionally used in solid dosage forms can also be included in the present technical solution of the present application.

The technical solution using the above carrier materials are: the composition contains from 1% to 50% by weight of, based on the weight of the composition, the active agent. It can be prepared as powders, granules, micro-pellets, tablets, lozenges, capsules. Preferably, the active agent is micronized to increase the degree of dispersion of the active agent so as to increase its dissolution surface, and to enhance dissolution ability. Some embodiments are provided as follows for exemplifying, wherein all of the percentages are by weight.

| (I) active agent | 1%-30% |
|---|---|
| lactose or glucose | 70%-99%. |

Preparation: the active agent and excipients are respectively crushed, and screened though 80-120 mesh sieves. Blend the active agent and lactose or glucose as recipe by quantity equivalent adding method increasingly to get a uniform mixture. The mixture is fractionally packed to obtain the powders. In this embodiment, appropriate amount correctant and preservative can be added if necessary.

| (II) Active agent | 5%-50%, |
|---|---|
| Disintegrant | 4%-8% |
| Binder | the appropriate amount |
| Filler | the balance amount of the composition |

Said disintegrant is selected from starch and cellulose derivatives, preferred sodium carboxymethyl starch. Said filler is selected from starch, microcrystalline cellulose, lactose or sucrose. Said binder is selected from starch paste or polyvidone.

Preparation: The active agent and excipients are respectively crushed, screened through 80-120 mesh sieves, and blended until uniform. The binder solution dissolved with water or organic solvent is added into the blend. They are agitated and kneaded to form soft material. The soft material is then granulated, dried, neatened, coated or uncoated. The obtained granule is fractionally packed. In this embodiment, appropriate amount of correctant and preservative can be further added, if necessary. Effervescent granules can be prepared by adding acid and base buffer agent.

| (III) Active agent | 5%-15% |
|---|---|
| Sodium carboxymethyl starch | 5%-20% |
| lubricants | 0.3%-3.0% |
| binder | appropriate amount |
| lactose | the rest of the composition |

The active agent and lactose is blended, preferably by the method of quantity equivalent adding. The active agent and lactose are mixed and crushed. The obtained mixture is screened through 80-100 mesh sieves. Sodium carboxymethyl starch is added into the mixture. They are blended them until uniform, wherein the method of quantity equivalent adding is also preferred. Binder is added. Kneading and granulating the kneaded agglomerate using oscillating granulator to obtain granules through screens of mesh 12-14. The wet granules is dried at 50-90° C., in which moisture should be less than 3% by weight. Blend the dry granules and lubricate until uniform, fill the blend into capsules at size 0 to 2. In this embodiment, PH101 or PH103 microcrystalline cellulose is preferred, magnesium stearate is adopted as lubricant, and PVPK30 dissolved in alcohol solution at appropriate concentration is selected as binder.

| (IV) Active agent | 5%-15%, |
|---|---|
| lactose | 25%-40%, |
| crospolyvinylpyrrolidone | 5%-15%, |
| magnesium stearate | 0-5%, and |
| microcrystalline cellulose | the rest of the composition |

The active agent microcrystalline cellulose, and lactose are blended and crushed. They are screened through 80-100 mesh sieves. The crospolyvinylpyrrolidone which has been crushed and screened through 80-100 mesh sieves is added, preferably by a method of quantity equivalent adding, until uniform. The mixture is directly compressed into tablets by ordinary rotary tablet pressing machine.

| (V) Active agent | 5%-15%, |
|---|---|
| hydroxypropylmethyl cellulose | 20%-40%, |
| sodium carboxymethyl starch | 5%-8%, |
| talc powder | 0-3%, |
| lactose | the rest of the composition |

The active agent, hydroxypropylmethyl cellulose, and lactose is blended and crushed. They are screened through 80-100 mesh sieves. The sodium carboxymethyl starch which has been crushed and screened through 80-100 mesh sieves is added. Blending the materiel until uniform, preferably using a method of quantity equivalent adding. Distilled water or starch paste is added into the mixture to form soft material. The granules through 20-50 mesh sieves are prepared from said soft material. The wet granules are dried at 50-90° C. The dried granules are filtered. The appropriate amount of lubricate is added therein. The obtained blend is compressed into tablets using ordinary rotary tablet pressing machine. Alternatively, they are filled into capsules at size 1 to 2. In this embodiment, lactose can be replaced by starch as filler, and sodium carboxymethyl starch can be replaced with crospolyvinylpyrrolidone as disintegrant whose proportion is 5%-15%.

Besides directly preparing compositions or preparations by using the above-mentioned carrier materials, micro-pellets technology is also applicable. For example, the active agent coats blank cores to obtain active micro-pellets; or the active agent and appropriate carriers are blended to form pellet cores. Said cores are further coated by a segregation layer. Micro-pellets containing the active agent obtained from any one of the above-mentioned method can also be coated by swelling layer(s), segregation layer(s), sustained-releasing layer(s) and so on, so as to control the agent releasing rate ideally. Carriers usually used in micro-pellet core or coating are selected from: sucrose, starch, dextrin, beeswax, fatty acid, shell-lac, povidone, methyl cellulose, cellulose acetate, polyacrylic acid, cellulose acetate phthalate (CAP), hydroxypropyl cellulose, polyethylene glycol, or mixture thereof. Micro-pellets can be dispensed directly for clinic usage, or be further made into capsules or tablets by adding appropriate excipients based on ordinary methods.

In above-mentioned technical solutions, the compressed tablets can be film coated, sugar coated or enteric coated. For instance, if the selected fillers or disintegrants are sensitive to moisture, film-coating materials possessing the function of moisture-segregating can be chosen for tablets' coating. Alternatively, a sugar coating is chosen for better taste of tablets.

Another technical solution of the present invention provides solid dosage forms that could be dispersed before taking orally, for instance, dispersible tablets, oral disintegration tablets, effervescent tablets, etc in pharmaceutics. This type of dosage form is very helpful to patients suffering from swallowing troubles. Besides one or more than one of the above-mentioned carriers, the disintegrating or dispersing abilities of the dosage forms could be by the follow technical solutions:

(I) Dispersible tablet: sufficient amount of disintegrant possessing good disintegrability is added so that the tablets can disperse rapidly in liquid. Preferred disintegrant is selected from crospolyvinylpyrrolidone, sodium croscarboxymethylcellulose, sodium carboxymethyl starch. The amount thereof should be sufficient to make tablets to be rapidly dispersed when contacting water. In order to disperse the dosage form rapidly, the compressibility, flowability, and disintegrability of fillers should be considered during the selection of the filler. The substance, such as microcrystalline cellulose, sodium carboxymethycellulose, hydroxypropyl methyl cellulose, or low-substituted hydroxypropyl cellulose can be used as the fillers having good properties.

(II) Oral disintegration tablets: sufficient amount of disintegrant possessing good disintegrability is added so that the tablets can disperse rapidly. Preferred disintegrant is selected from crospolyvinylpyrrolidone, sodium croscarboxymethylcellulose, sodium carboxymethyl starch. The amount thereof should be sufficient to make tablets to be rapidly dispersed when contacting water. In order to disperse the dosage form rapidly, the compressibility, flowability, and disintegrability of fillers should be considered during the selection of the filler. The substance, such as microcrystalline cellulose, sodium carboxymethycellulose, hydroxypropyl methyl cellulose, or low-substituted hydroxypropyl cellulose can be used as the fillers having good properties.

(III) Effervescent tablet: the substance for producing $CO_2$ upon contacting water, i.e., effervescent agent, is added. The invention composition comprises the effervescent agent selected from the combination of sodium bicarbonate and organic acids such as tartaric acid or malic acid, the combination of phosphates, or organic acid anhydrides, such as succinic anhydride, citric anhydride. The usage thereof can also achieve the purpose of dispersing tablets rapidly. This kind of tablets, named as effervescent tablets, can be directly swallowed, or dispersed in water before taking orally. It is very helpful for patients who are not accustomed to taking solid dosage forms, such as capsules, tablets, lozengeles, etc. An embodiment is: active ingredient, microcrystalline cellulose, croscarmellose sodium, povidone, fine powder of sucrose, saccharin sodium, malic acid, sodium bicarbonate, exsiccated sodium carbonate, sodium lauryl sulphate, flavors.

Preparing: Sodium bicarbonate is sieved through 30 mesh screen; anhydrous sodium carbonate, sodium lauryl sulphate, and essence are sieved through 60 mesh screen for standby. The active agent and MCC are blended, crushed and sieved through 80 mesh screen. Croscarmellose sodium, malic acid, sucrose are crushed and sieved through 30 mesh screen. They are blended with saccharin sodium. The blended material is granulated with polyvidone-isopropanol solution. The granule is dried, and sieved through 30 mesh screen. The sieved dry granules are blended with the remaining components, and compressed into tablets by means of ordinary tabletting machines.

In the formulations of above-mentioned tablets, oral disintegration tablets, effervescent tablets, the diameter of particulates after disintegration is controlled no more than 400 nm. During the preparation, granulation is not an essential procedure, and direct tabletting is the preferred means. Similarly, if the diameter of aforementioned micro-pellets is too small to bring any sandy taste, as average particle diameter is less than 400 nm, the micro-pellets can be used for this preparation dispersed before swallowing. Correctants or other excipients can be included in these dosage forms for good taste.

Pharmaceutical Compositions Containing Solubilizing Carriers

Another aspect of the present invention provides a pharmaceutical composition containing pharmacologically active agent and solubilizing carriers. That is, first of all, the active agent is dispersed into pharmaceutically acceptable carriers to enhance the dissolution of the active agent. Said carriers used in the present application are called solubilizing carriers. Solubilizing carriers in the present invention are preferentially selected from the group consisting of PEGs, polyvidones, surfactants containing polyoxyethylene group, water-soluble cellulose derivatives, organic acids, saccharides and alcohols. The carrier can be used alone or in combined form.

The exemplified solubilizing carriers are described as follows for detailed illustration. However, they do not intend to limit the present invention. Based on the embodiments in the present invention, the technical solutions, wherein the formulations can be simply altered, and the processes for the preparation thereof can be optimized, carrier materials and preparing methods are replaceable, should also be included in the present invention therefor.

(I) Polyethylene Glycol (PEG) as Solubilizing Carriers

Polyethylene glycol (PEG) possesses good solubility in water. It can also be dissolved in many kinds of organic solvents. When the active agent is dispersed therein, PEGs can make the active agent highly dispersed in it. Furthermore, its viscosity increases due to the evaporation of solvent during preparing procedure, which can prevent the active agent from assembling. The molecular weight of PEG used for solid dispersion is usually between 1000-20000. One of PEG2000, PEG4000, PEG6000, PEG10000, PEG12000, PEG20000, or a mixture thereof is in common use. Polyoxyethylene(40) monostearate, stearic acid, or surfactants of poloxamer are commonly used in combination With PEGs to adjust the dispersity and the release of the active agent. The dosage form can be made by dropping methods when the active agent is dispersed in these carriers. For example, the dripping pills containing the active agent and PEG as main carrier can be prepared by means of drip pilling machine.

An embodiment using PEGs as solubilizing carriers read as follows: the active agent and carriers are weighed according to the following proportions by weight: 1%-8% of the active agent, 10%-20% of PEG4000, 60%-70% of PEG6000, 3%-5% of poloxamer 188. The active agent is comminuted and sieved through 80 mesh screen. The screened active agent is added into other carriers melted in water bath at 80-90° C. The mixture is stirred to be uniform. When the active agent powder disappears completely, the melted liquid containing the active agent is charged into the incubator of the drip pilling machine. Adjust the dripping rate to 20-30 drops per minute into the liquid coolant. The coolant is selected from simethicone or liquid olefin, and the cooling temperature is 4-10° C. The obtained drips are collected. The liquid coolant on the surface of drips is wiped out by absorptive paper, and the obtained drips are placed in refrigeratory with keeping under 4° C. for 24 hours. The drips can be directly taken orally. It is testified by dissolution tests that the obtained drips can be dispersed rapidly. Therefore, it is very suitable to apply sublingually so as to be quickacting.

Another embodiment is: the active agent and PEG6000 is mixed in the ratio of 1:1 by weight. The conventional amount of fillers, disintegrants are added. The obtained mixture is compressed into tablets.

(II) Povidone and/or Crospovidone as Solubilizing Carriers

Povidone is 1-ethylene-2-pyrrolidone homopolymer (Polyvinylpyrrolidone; Povidone; Plasdone; Kollidone; PVP for short hereinafter), such as PVPk12, PVPk15, PVPk17, PVPk25, PVPk30, PVPk29/32, PVPk60, PVPk90, PVPk120, etc. Crospovidone (PVPP) is synthesized cross-N-ethylene-2-pyrrolidone homopolymer, such as PVPPXL, PVPPXL-10, etc. The two kinds of materials can be individually or jointly used as solubilizing carriers. The processes for the preparation thereof can be solvents method, solvent depositing method, spray drying method, or freeze drying method, etc. The combination of povidone and crospovidone can be illustrated as following.

PVPk29/32 and PVPPXL as carriers in the ratio of 1:1-3:7 by weight, and the ratio of drug and carriers is 1:2-1:10. Preparation: the active agent and PVP29/32 are dissolved in the mixed solvent of alcohol and acetone. The obtained solution is sprayed onto PVPPXL by means of fluid bed, or the obtained solution is directly dried by spray drying. Another preparation embodiment is: the active agent and the carriers in the above-mentioned ratio are dispersed into proper solvent system, and dry powder is obtained by using freeze drying art.

PVPk29/32 and PVPPXL as carriers are in the ratio of 1:2-1:3 by weight, and the ratio of the active agent and carriers is 1:1-1:2. Preparing: the active agent and PVP29/32 are dissolved in the mixed solvents of alcohol, acetone and water (4:4:1). The obtained solution is sprayed onto PVPPXL by means of fluid bed to obtain dry solubilizing composition. After sieving, the appropriate excipients are added to make powders, granules, capsules or tablets. Another preparation embodiment is: the active agent and carriers in the above-mentioned ratio are dispersed in a proper solvent system. A dry powder is obtained by using freeze drying art.

(III) Cellulose Derivatives as Solubilizing Carriers

Cellulose derivatives can also be used as solubilizing carriers. In one embodiment, hypromellose (HPMC) and polyoxyethylene polyoxypropylene glycol are used as carrier materials. The ratio of the active agent, HPMC, polyoxyethylene polyoxypropylene glycol by weight is 1:3-5:0.2-0.5. HPMC and polyoxyethylene polyoxypropylene glycol are dissolved in the mixture of ethanol/acetone/water. The active agent is added therein. They are mixed to be uniform. The obtained solution is sprayed onto the blank pellet cores in fluid bed to obtain the granules of solid dispersing composition. In this embodiment, solvent is selected from the group consisting of methanol, ethanol, isopropyl alcohol, acetone, dichlormethane, water, and mixture thereof.

(IV) Saccharides and/or Alcohols as Solubilizing Carriers

Saccharides and/or alcohols used as solubilizing carriers can be: dextrose, galactose, sucrose, mannitol, sorbitol, xylitol, etc. There are multiple hydroxyls in the molecular structure of these materials, which can be combined with the active agent via hydrogen bond. In light of the active agent in the present invention, mannitol is preferred as main carrier.

(V) Other Carriers

It is known in this art that the solubilizing carriers are not limited to the above-mentioned materials. Others, such as hydrolyzable glutin and surfactants, are also applicable in the present invention. Even choosing hard soluble carrier materials or lipid materials, such as ethylcellulose, acrylic resin E, RL, RS, cholesterol, carnauba, etc, solubilizing but non-quick releasing composition can be prepared by adding water-soluble carrier materials such as PEG, PVP. These sustained or controlled releasing dosage form is useful for maintaining long term release of the active agent as indicated by the existing pharmaceutical research.

The above-mentioned solubilizing compositions such as drips, can be directly administrated, or be intermediates for the preparation of the dosage forms. The other solid dosage forms, such as powders, granules, micro-pellets, tablets, capsules, lozengeles, etc., can be prepared by adding pharmaceutically acceptable carriers. The pharmaceutically acceptable carriers include, but not limited to, the above-mentioned excipients, for example, starch and its derivatives, cellulose derivatives, sucrose, mannitol, sillicic acid, calcium hydrogen phosphate as fillers; MC, HPC, glutin, PVP as binders; croscarmellose sodium, PVPP, L-HPC as disintegrants; magnesium stearate, talc powder as lubricants, and stevioside, aspartame and other essences as correctants. Directly compressed tablets is a preferred process when preparing tablets. Optional excipients include fillers, disintegrants, lubricants and other added excipients such as glidants and correctants and so on, if necessary, which are suitable for directly compressing tablets. Optional fillers may be MCC and/or lactose, whose percentage in formulation is 20%-90%. Disintegrants can be selected from cross-carboxymethyl starch sodium, crospolyvinylpyrrolidone, L-HPMC, etc., whose percentage in formulation is 1%-6%. The tablets can be film-coated, or sugar-coated if necessary.

In one embodiment, the obtained solubilizing composition is prepared to capsules. The added filler is selected from MCC, starch, CMS-Na, PVPP; the amount thereof in the formulation is 60%-95%. The added glidants and lubricants are selected from talc powders, magnesium stearate, aerosil, or mixture thereof; the amount thereof in the formulation is 0-3%. The solubilizing carrier containing the active agent obtained according to the above-mentioned technical solution takes 5%-40% of the total weight of the formulation. The solubilizing composition is comminuted and sieved through a 60 mesh screen, blended with excipients uniformly. The obtained mixture is filled into hard capsules of size 1 or 2 made of glutin shells.

Another embodiment is: the solubilizing composition is prepared from the active agent and povidone K29/32, PVP-PXL, in which the active agent weighs 8%-30% wt. The solubilizing composition is further prepared to tablets. The amount of solubilizing composition in tablet is 35%-65% based on the total weight of tablet, the amount of filler as MCC is 10%-40% based on the total weight of tablet, and the amount of disintegrant as PVPP is 5%-8% based on the total weight of tablet. The remaining materials are excipients as lubricants, and so on. One method for the preparation thereof is: the active agent, povidone K29/32 and PVPPXL are dissolved in the appropriate amount of solvent made of acetone and alcohol (ratio by volume is 1:1). The solution is spray using spray gun into fluid bed in top-spraying mode to granulate. Dry the wet granules and blend with other excipients uniformly. The obtained mixture is pressed to tablets directly.

Another embodiment is: solubilizing composition is prepared from the active agent, povidone K29/32 and PVPPXL, in which the amount of the active agent is 8%-30% based on the total weight of the composition. The ratio of povidone K29/32 to PVPPXL is 1:2-1:3 by mass. The solubilizing composition is prepared according to above-mentioned method. It is comminuted and sieved. The filler such as MCC, accounting for 40%-60% based on the total weight of the composition, disintegrant as PVPP, accounting for 1%-6% based on the total weight of the composition, and the rest amount of excipients such as lubricant are added therein. In one process for the preparation thereof, the active agent, povidone K29/32 and PVPPXL is dissolved in appropriate amount of mixed solvent consisting of acetone, alcohol and water (ratio by volume is 4:4:1). The obtained solution is sprayed into fluid bed in top-spraying mode to granulate. Dry the wet granules and blend with other excipients uniformly. The obtained mixture is pressed into tablets directly. The solubilizing composition is further prepared to tablet. The amount of the solubilizing composition is 35%-65% based on the total weight of tablet.

In another embodiment, a solubilizing composition is prepared from the active agent, povidone K29/32 and PVPPXL, in which the ratio of povidone K29/32 and PVPPXL by weight is 1:2-1:3, and the percentage of the active agent in composition occupies 30%-40% wt. The solubilizing composition is further prepared into tablets. The amount of filler as MCC is 25%-35% based on the weight of the composition, and the amount of disintegrant as PVPP is 1%-5% based on the weight of the composition. The remaining materials are other excipients as lubricants and so on. In one preparing method, the active agent, povidone K29/32 and PVPPXL is dissolved in appropriate amount of mixed solvent made of acetone, ethanol and water (ratio by volume is 4:4:1). The solution is sprayed into fluid bed in top-spraying mode for granulating. Dry the wet granules and blend them with other excipients uniformly, press the obtained mixture into tablets directly.

In the pharmaceutical composition of the present invention, the content of pharmacological active agent can be 5 mg-180 mg, preferred one third, a half or multiple of the daily dosage for human being. If calculating according to animal tests by the general conversing method of animal's effective dosage to human being's effective dosage, the content could be 5 mg, 10 mg, 20 mg, 30 mg, 40 mg, 50 mg, 60 mg, 70 mg, 80 mg, 90 mg, 100 mg, 120 mg, 140 mg, 160 mg, 180 mg.

The pharmaceutical composition or the dosage form in the present invention can be used as cardiovascular medicaments, especially antihypertension medicaments. The medicaments can be orally or sublingually administered to human being.

The dissolubility test for the solid preparation forms of pharmaceutical compositions in the present invention has been carried out according to the second method of dissolubility testing methods in the 2005 edition of Chinese pharmacopoeia, appendix XC. Dissolution solvent is 900 ml of pH 6.8 phosphate buffer solution, at constant temperature of 37° C., and the rotate speed is 50 r/m. Sample at 45 min, assay the drug content using ultraviolet spectrophotometry, calculate the dissolubility of drug. The results indicate that the solid dosage form containing the invention solubilizing composition have predominant dissolubility.

Using ordinary pharmacological experiments methods, the absorption test of beagle dogs for the solid dosage forms of pharmaceutical compositions in the present invention has been carried out. The results indicate that the absorption degree of the active agent in the dosage form, especially the solid dosage form containing solubilizing carrier. is better than that in suspending solution.

The invention is further illustrated by the following examples. It is appreciated that these examples are only intended to illustrate the invention, but not to limit the carriers, preparing methods and uses.

Besides oral or sublingual administration, the pharmacologically active agent in the invention can be administered by other methods, such as injection, transdermal delivery, inhalation, etc. These administration methods have unique clinic requirements. Formulations and preparing of these dosage form could be the same as those of ordinary injection, transdermal delivery, inhalation dosage form. Beside oral dosage form, other dosage form containing pharmacological active agent in the invention are also included in the scope of the present invention.

The pharmaceutical composition in the invention could be used as cardiovascular drugs, especially antihypertension drugs. The methods comprise administering the pharmaceutical composition containing effective amount of pharmacological active agent. Preferably, the pharmaceutical composition is administered once daily. The pharmaceutical composition could also be administered in combination with other antihypertension drugs for reducing hypertension more effectively. Said other antihypertension drugs include diuretic agent such as hydrochlorothiazide, angiotensin converting enzyme inhibitor, calcium antagonist, etc. Preferably combine with the drugs possessing different antihypertensive mechanism.

MODE OF CARRYING OUT THE INVENTION

The following examples are merely illustrative of the invention and are not intended to limit the scope of the invention.

EXAMPLE 1

Preparation of Compound I 2-butyl-4-chloro-1-[2'-(1H-tetrazol-5-yl)1,1'-biphenyl-methyl]imidazole-5-carboxylic acid, 1-[(isopropoxy)carbonyloxy]methyl ester To a 100 ml of one-necked flask, 0.523 g of 2-butyl-4-chloro-1-[2'-(1-tri-benzyl-tetrazol-5-yl) 1,1'-biphenyl-methyl]imidazole-5-carboxylic acid, 0.124 g of potassium carbonate, 5 ml of N,N-dimethylacetamide were added in turn. The solution was stirred at room temperature for 20 minutes. Then 0.562 g of 1-chloromethyl isopropyl carbonate was added and the mixture was reacted at 45-50° C. for 16 hours. After the reaction was completed, the mixture solution was filtered, and 30 ml of water was added into the filtrate. The resulting mixture was extracted with 30 ml of ethyl acetate twice. The organic phase was dried and concentrated to give 1.724 g of oil, which was directly used in the next reaction without purification.

10 ml of dioxane and 5 ml of 4 mol/L HCl were added, and the resulting mixture was reacted at room temperature for 16 hours. The reaction was stopped and the solution was adjusted to pH 6-7 using aqueous sodium bicarbonate solution. The solution went turbid, and was extracted with ethyl acetate. The organic phase was washed with saturated brine, dried, concentrated to give 0.436 g of 2-butyl-4-chloro-1-[2'-(1H-tetrazol-5-yl) 1,1'-biphenyl-methyl]imidazole-5-carboxylic acid, 1-[(isopropoxy)carbonyloxy]methyl ester.

The structure's spectrum data of the compound is as below:
$^1$H-NMR (CDCl$_3$) δ H (ppm): 0.89 (t, 3H, J=14.6), 1.24 (d, 6H, J=6.3), 1.37 (m, 2H, J=22.1), 1.69 (m, 2H, J=30.5), 2.64 (t, 2H, J=15.5), 4.81 (m, 1H, J=12.4), 5.54 (s, 2H), 5.86 (s, 2H), 6.95-7.64 (8H), 8.08 (d, 1H, J=7.42)

ESI(+)m/z: 552.7

Mp: 134.5-136° C.

Research on Pharmacological Effect and Related Pharmaceutical Applications (I) Beagle dogs are selected as experimental animals, six dogs per group. 2-butyl-4-chloro-1-[2'-(1H-tetrazol-5-yl) 1,1'-biphenyl-methyl]imidazole-5-carboxylic acid, 1-[(isopropoxy)carbonyloxy]methyl ester suspended in physiologic saline is administered in single dose of drug by gavage in dosage level of 3.0 mg/kg, 9.0 mg/kg, and 27 mg/kg. Blood samples were drawn for each dosage group at set time point. Separate and prepare the blood plasma, detect by LC-MS method and get known that the drug is converted into its active metabolite EXP3174 (2-butyl-4-chloro-1-[2'-(1H-tetrazol-5-yl) 1,1'-biphenyl-methyl]imidazole-5-carboxylic acid). Determine the level of the active metabolite in plasma, calculate EXP3174's pharmacokinetic parameters according to the concentration-time curve, and investigate the correlation between dosage and main pharmacokinetic parameters Cmax and AUC0-t. It was discovered that the value Cmax and AUC0-t was proportional to the dosage.

(II) spontaneously hypertensive rat (SHR) is administrated 15 mg/kg or 30 mg/kg of 2-butyl-4-chloro-1-[2'-(1H-tetrazol-5-yl) 1,1'-biphenyl-methyl]imidazole-5-carboxylic acid, 1-[(isopropoxy)carbonyloxy]methyl ester dispersed into physiologic saline by gavage, and the blood pressure decrease 10 mm and 20 mm of mercury column after administering the agents respectively. The results show that the compound has significant antihypertensive effect to rats when the oral dosage is no less than 15 mg/kg.

Preparation of Compositions Containing 2-butyl-4-chloro-1-[2'-(1H-tetrazol-5-yl) 1,1'-biphenyl-methyl]imidazole-5-carboxylic acid, 1-[(isopropoxy)carbonyloxy]methyl ester

EXAMPLE A1

Formulation: the active agent 4 g, lactose 36 g.

Preparation: the active agent is ground and passed through 120 mesh sieve. The lactose passes through 80 mesh sieve. The amount of lactose in formulation is equivalent-increasingly blended with the active agent to get a uniform mixture. The obtained mixture is subpackaged to obtain the powders of the active agent. In this example, appropriate amount flavoring agents, flavors and preservatives can be added if necessary.

EXAMPLE A2

Formulation: active agent 5 g, starch 15 g, sucrose 10 g, sodium carbomethyl starch 2 g, appropriate amount of 70% starch paste.

Preparation: the active agent and other excipients are ground respectively. The active agent is ground and passed through 120 mesh screen, and other excipients through 80 mesh screen. Blend the active agent, starch, lactose and sodium carbomethyl starch uniformly. The appropriate amount of 70% starch paste is added. Knead the obtained mixture. Granulate using 14 mesh screen, dry at 60° C., and sieve the dry granules using 12 mesh screen. The mixture is subpackaged to obtain the granules of the active agent. In this example, appropriate amount flavoring agents, flavors and preservatives can be added if necessary.

EXAMPLE A3

Formulation: active agent 5 g, microcrystalline cellulose 20 g, lactose 20 g, sodium carbomethyl starch 5 g, magnesium stearate 1 g, PVPk30 proper amount.

Preparation: the active agent and lactose are blended. They are ground and passed through 80-100 mesh screen. The microcrystalline cellulose ground and passed previously through 80 mesh screen, sodium carbomethyl starch are added. 5%-20% of PVPk30 ethanol solution is added into the mixture to prepare the soft material. Granulate the kneaded agglomerate using oscillating granulator to obtain granules through screens of mesh 12-14. Dry the wet granules at 50-90° C., in which moisture should be less than 3% by weight. Blend the dry granules and lubricate until uniform, fill the blend into capsules of size 1. The tested dissolution rate of obtained capsules is 76.6% at 45 minutes.

EXAMPLE A4

Formulation: the active agent 4 g, microcrystalline 15 g, lactose 15 g, PVPPXL 5 g, magnesium stearate 1 g.

Preparation: the active agent and excipients are sufficiently ground and uniformly blended. They are directly compressed into tablets. The tested dissolution rate of obtained tablets is 71.9% at 45 minutes.

EXAMPLE A5

Formulation: the active agent 5 g, lactose 29 g, hypromellose 15 g, sodium carbomethyl starch 4 g, magnesium stearate 1 g.

Preparation: the active agent and excipients are dried at 60° C. The active agent and lactose are blended and completely ground. They pass through 80 mesh screen. Hypromellose and sodium carbomethyl starch are added and uniformly blended. The proper amount of distillate water is added into the mixture. Knead and granulate using 24 mesh screen. The wet granules are dried at 60° C. by hot air, and sieved through 14 mesh screen. The magnesium stearate is added and blended uniformly. The obtained mixture is pressed into tablets. 45-minute dissolution rate of the tablets is 75.5%.

EXAMPLE A6

Formulation: active agent 4 g, starch 15 g, hypromellose 12 g, PVPPXL 4 g, magnesium stearate 0.5 g, 7% starch paste proper amount.

Preparation: the active agent and excipients are dried at 60° C. The active agent and starch are mixed and sufficiently ground. They pass through 100 mesh screen. Hypromellose and PVPPXL are added and blended uniformly. Add proper amount of 7% starch paste into the blend. Knead and granulate using 14 mesh screen. The wet granules are dried at 60° C. by hot air. Magnesium stearate is added into the dry granules. Mix and sieve the mixture, fill the sieved mixture into hard capsule of size 1. 45-minute dissolution rate of the capsules is 74.8%.

EXAMPLE A7

Pellet core formulation: active agent 5 g, microcrystalline cellulose 20 g, low-substituted hydroxypropyl cellulose 10 g, magnesium stearate 1 g, sodium dodecylsulphate 1 g.

The formulation of the coating solution for segregation layer: hypromellose (Pharmacoat 606) 13 g, PEG 400 2.6 g, talc powder 6.5 g, suitable amount of water Preparation: the active agent is ground and passed through 80 mesh screen. Excipients are ground and passed through 60 mesh screen. Dissolve the sodium dodecylsulphate into suitable amount of water. Blend the active agent, microcrystalline cellulose, low-substituted hydroxypropyl cellulose and magnesium stearate uniformly, knead the blend using sodium dodecylsulphate solution, and prepare micropellets using extruding and rolling machine. The pellets are dried at 60° C., and sieved. Sieved pellets between 18-24 mesh are coated with segregation coating by fluid bed.

Dissolve the hypromellose into water, and add PEG 400 into it. Disperse the talc powder into the solution to prepare the coating solution of segregation layer. Coat the obtained pellets using fluid bed in the mode of bottom spraying, the weight increasing rate of coating is 4%. The pellets coated by segregation layer are dried at 40° C. for 30 minutes. The dissolution rate of pellets in 45 minutes is 84.5%.

EXAMPLE A8

Formulation: blank pellet cores 60 g, the active agent 10 g, hypromellose 603 10 g, low-substituted hydroxypropyl cellulose 3 g, water proper amount.

Preparation: Hypromellose 603 is dissolved in water, and the active agent is ground and passed through 80 mesh screen. The ground active agent and low-substituted hydroxypropyl cellulose is dispersed into the water solution of hypromellose 603. The blank pellet cores is charged into a fluid bed, coated with the active agent solution. The obtained pellets are filled into gel hard capsules. The dissolution rate of obtained capsules in 45 minutes is 74.5%

EXAMPLE B1

Formulation: active agent 5 g, mannitol 10 g, microcrystalline cellulose 10 g, PVPPXL 2.25 g, magnesium stearate 0.25 g, lemon essence 0.12 g, aspartame 0.12 g, talc powder 0.2 g.

Preparation: The active agent and mannitol are blended and ground. The obtained mixture passes through 80 mesh screen. Other components are ground and sieved through 60 mesh screen. All of the components are uniformly blended. The obtained mixture are directly compressed into tablets. The obtained tablets disintegrate within 3 minutes in 5 ml distilled water. And dissolution rate tested by the above-mentioned method is 64.5% in 45 minutes.

EXAMPLE B2

Formulation: active agent 20 g, tartaric acid 50 g, sodium bicarbonate 56 g, carboxymethyl cellulose 20 g, microcrystalline cellulose 30 g, talc powder 6 g, magnesium stearate 2 g.

Preparation: The active agent, tartaric acid, carboxymethyl cellulose, microcrystalline cellulose are blended and sieved through 16 mesh screen. Granulate using 7% PVP-isopropyl alcohol solution, dry, and sieve the granules by 30 mesh screen. Sodium bicarbonate is ground and sieved through 30 mesh screen. Blend the obtained granules with sieved sodium bicarbonate, add talc powder, magnesium stearate into it, blend uniformly, and press the mixture into tablets. Thereby effervescent tablets are obtained. The dissolution in 45 minutes is 64.5%.

EXAMPLE C1

Formulation: active agent 10 g, PEG400 10 g, PEG6000 60 g, Poloxamer 188 5 g, stearic acid 5 g.

Preparation: the active agent is ground and sieved through 80 mesh screen, and then is added into the remaining matrixes fused by water bath heating at 80-90° C. Agitate the components until the active agent powder disappears completely to form a uniform mixture. The fused liquid containing the active agent is charged into incubator of drip pilling machine. Adjust the dripping rate to 20-30 drops/minute into liquid coolant. The cooling agent is selected from dimeticone or liquid paraffin. Cooling temperature is 4-10° C. The obtained dropping pills are collected. The liquid coolant on the surface of pills are wiped out by absorptive paper. After being kept in refrigeratory at 4° C. for 24 hours, the drips is obtained. It is testified by dissolution tests that the obtained drips can be dispersed and dissolved rapidly within 15 minute. Therefore, the obtained drips are very suitable to be sublingually administered to achieve quickly curative effect.

EXAMPLE C2

Formulation: active agent 2 g, PEG12000 20 g, PEG6000 60 g, Poloxamer 188 6 g.

Preparation: the active agent is ground and sieved through 80 mesh screen, and then is added into the remaining matrixes fused by water bath heating at 80-90° C. Agitate the components until the active agent powder disappears completely to form a uniform mixture. The fused liquid containing the active agent is charged into incubator of drip pilling machine. Adjust the dripping rate to 20-30 drops/minute into liquid coolant. The cooling agent is selected from dimeticone or liquid paraffin. The cooling temperature is 4-10° C. The obtained dropping pills are collected. The liquid coolant on the surface of pills are wiped out by absorptive paper. After being kept in refrigeratory at 4° C. for 24 hours, the drips is obtained. It is testified by dissolution tests that the obtained drips can be dispersed and dissolved rapidly within 5 minute. Therefore, the obtained drips are very suitable to be sublingually administered to achieve quickly curative effect.

EXAMPLE D1

Formulation: active agent 5 g, PVPk29/32 36 g, microcrystalline cellulose 20 g, lactose 20 g, PVPPXL 4 g, magnesium stearate 4 g.

Preparation: the active agent and PVPk29/32 are dissolved into appropriate amount of ethanol. The obtained solution is sprayed and dried. The dried product is mixed with the other excipients uniformly. The obtained mixture is compressed into tablets. The dissolution of obtained tablets in 45 minutes is 95.5%.

EXAMPLE D2

Formulation: active agent 5 g, PVPPXL(A) 20 g, microcrystalline cellulose 20 g, lactose 20 g, PVPPXL(B) 4 g, magnesium stearate 4 g.

Preparation: the active agent is dissolved into appropriate amount of acetone. PVPPXL(A) is added into the prepared solution to mix uniform. The sample is dried under reduced pressure. The dried product is uniformly mixed with the other excipients. The obtained mixture is compressed into tablets. The dissolution of obtained tablets in 45 minutes is 96.8%.

EXAMPLE D3

Formulation: active agent 5 g, PVPk29/32 10 g, PVPPXL(A) 26 g, microcrystalline cellulose 10 g, lactose 10 g, PVPPXL(B) 3 g, sodium stearoyl fumarate 0.5 g.

Preparation: the active agent and PVPk29/32 are dissolved into appropriate amount of a mixed solution of acetone and ethanol (ratio of volume is 1:1). PVPPXL(A) is placed into a fluid bed. The prepared solution is sprayed into the fluid bed in top-spraying mode to granulate. The wet granules are dried, and then blended with the other excipients uniformly. The obtained mixture is compressed into tablets. The dissolution of obtained tablets in 45 minutes is 96.7%.

EXAMPLE D4

Formulation: active agent 15 g, PVPk29/32 20 g, PVPPXL(A) 20 g, microcrystalline cellulose 10 g, lactose 10 g, PVPPXL(B) 2.5 g, sodium stearoyl fumarate 0.4 g.

Preparation: the active agent and PVPk29/32 are dissolved into appropriate amount of a mixed solution of acetone and ethanol (ratio of volume is 1:1). PVPPXL(A) is placed into a fluid bed. The prepared solution is sprayed into the fluid bed in top-spraying mode to granulate. The wet granules are dried, and then blended with the other excipients uniformly. The obtained mixture is compressed into tablets. The dissolution of obtained tablets in 45 minutes is 98.5%.

EXAMPLE D5

Formulation: active agent 15 g, PVPk29/32 8 g, PVPPXL(A) 20 g, microcrystalline cellulose 10 g, lactose 10 g, PVPPXL(B) 2.5 g, sodium stearic acyl fumarate 0.4 g.

Preparation: the active agent and PVPk29/32 are dissolved into appropriate amount of a mixed solution of acetone and ethanol (ratio of volume is 1:1). PVPPXL(A) is placed into a fluid bed. The prepared solution is sprayed into the fluid bed in top-spraying mode to granulate. The wet granules are dried, and then blended with the other excipients uniformly. The obtained mixture is compressed into tablets. The dissolution of obtained tablets in 45 minutes is 97.8%.

EXAMPLE D6

Formulation: active agent 15 g, PVPk29/32 23 g, PVPPXL(A) 23 g, microcrystalline cellulose 10 g, lactose 10 g, PVPPXL(B) 2.5 g, sodium stearoyl fumarate 0.4 g.

Preparation: the active agent and PVPk29/32 are dissolved into appropriate amount of a mixed solution of acetone and ethanol (ratio of volume is 1:1). PVPPXL(A) is placed into a fluid bed. The prepared solution is sprayed into the fluid bed in top-spraying mode to granulate. The wet granules are dried, and then blended with the other excipients uniformly. The obtained mixture is compressed into tablets. The dissolution of obtained tablets in 45 minutes is 98.3%.

EXAMPLE E1

Formulation: active agent 10 g, microcrystalline cellulose (A) 20 g, microcrystalline cellulose (B) 10 g, lactose 10 g, sodium carboxymethyl starch 2.5 g, stearic acid 0.4 g.

Preparation: the active agent and microcrystalline cellulose (A) are ground and mixed together for 20 minutes. The obtained mixture is then blended with the other excipients. Then the mixture are compressed into tablets. The dissolution of the obtained tablets in 45 minutes is 86.7%.

EXAMPLE F1

Beagle dogs are selected as experimental animals, six dogs per group. The suspension containing the raw material of the active agent, dosage forms in examples A1 and D3 are administered by gavage in single dose of 9.0 mg/kg. Blood samples were drawn for each group at the given time point. The blood plasma is separated and prepared. The plasma level of the active metabolite EXP3174 is determined by liquid chromatogram-tandem mass spectrometry. The pharmacokinetic parameters of EXP3174 are calculated according to the concentration-time curve. The results are shown as table 1. It is known from the results: When the same dose of the active agent is orally administered to the beagle dogs, the absorption of the active agent in each dosage form is better than that in the suspension in the raw material form; and the absorption degree of the dosage form containing solubilizing carriers is greater than that in the ordinary dosage forms.

TABLE 1

The results of the absorption of the active agent in the animal

| pharmacokinetic parameters | Groups of animals | | |
|---|---|---|---|
| | Suspension containing the active agent | Dosage form in example A1 | Dosage form in example D3 |
| AUC0-t(ng · h/ml) | 651 ± 230 | 890 ± 258 | 1122 ± 344 |
| AUC0-∞(ng · h/ml) | 671 ± 236 | 916 ± 276 | 1174 ± 390 |
| Cmax(ng/ml) | 208 ± 123 | 362 ± 169 | 574 ± 278 |
| Tmax(h) | 2.60 ± 0.89 | 2.0 ± 0.80 | 1.50 ± 0.77 |

The invention claimed is:

1. A pharmaceutical composition comprising 2-butyl-4-chloro-1-[2'-(1H-tetrazol-5-yl) 1,1'-biphenyl-methyl]imidazole-5-carboxylic acid, 1-[(isopropoxy)carbonyloxy]methyl ester as a pharmacological active agent, and a pharmaceutically acceptable carrier.

2. The pharmaceutical composition according to claim 1, wherein the amount of the pharmacological active agent is 1%-50% by weight based on the total weight of the composition.

3. The pharmaceutical composition according to claim 2, wherein the carrier is one or more than one substances selected from the group consisting of filler, disintegrants, wetting agent, binder, lubricant, surfactants, glidant, flavoring agent, flavor, colorant, and the mixture thereof.

4. The pharmaceutical composition according to claim 3, wherein the filler is one or more than one selected from the group consisting of calcium carbonate, magnesium carbonate, calcium phosphate, calcium sulfate, magnesium oxide, calcium carboxymethylcellulose, sodium carboxymethylcellulose, sucrose, lactose, fructose, xylitol, starch or its derivates, dextrin, microcrystalline cellulose, and the mixture thereof; the disintegrant is one or more than one substances selected from the group consisting of starch, alginic acid, calcium carboxymethylcellulose, sodium carboxymethylcellulose, croscarmellose sodium, crospolyvinylpyrrolidone, low-substituted hydroxypropyl methylcellulose (hypromellose), microcrystalline cellulose, methyl cellulose, and the mixture thereof; the wetting agent is one or more than one substances selected from the group consisting of distilled water, ethanol, starch paste, and the mixture thereof; the binder is one or more than one selected from the group consisting of acacia, gelatin, tragacanth, dextrin, polyvinylpyrrolidone, starch and the derivative thereof, sodium alginate, sorbitol, syrup, hypromellose, methyl cellulose, hydroxypropyl cellulose, hydroxyethylcellulose, ethylcellulose, sodium carboxymethylcellulose, calcium carboxymethylcellulose, glucose, polymethacrylate, and the mixture thereof; the lubricant is one or more than one substances selected from the group consisting of calcium stearate, glyceryl monostearate, palmityl glyceryl stearate, magnesium stearate, microcrystalline cellulose, sodium benzoate, sodium chloride, sodium dodecylsulfate, sodium stearyl fumarate, talc powder, zinc stearate, polyethylene glycol, and the mixture thereof; the surfactant is one or more than one substances selected from the group consisting of sodium dodecylsulfate, poloxamer, Tweens, bromination hexadecane trimethylamine, Sodium Laurylsulfate, sodium stearyl alcohol sulphate, polyoxyethylene high-grade fatty alcohol, sucrose esters, sorbitol fatty ester, soybean phospholipid, and the mixture thereof; the glidant is one or more than one selected from the group consisting of colloidal silicon dioxide, powdered cellulose, magnesium trisilicate, silicon dioxide and talc powder, and the mixture thereof.

5. The pharmaceutical composition according to claim 3, wherein the carrier further comprises an effervescent agent, selected from sodium bicarbonate, phosphates, organic acids, organic anhydrides and the mixture thereof.

6. The pharmaceutical composition according to claim 1, wherein the carrier further comprises a solubilizing carrier, in which the pharmacologically active agent is dispersed, said solubilizing carrier is selected from the group consisting of polyethylene glycol, povidone, surfactants comprising polyoxyethylene group, water-soluble cellulose derivatives, organic acids, saccharides, sterols, lipides and the mixture thereof.

7. The pharmaceutical composition according to claim 6, wherein the solubilizing carrier is selected from the group consisting of polyethylene glycol, povidone, surfactant comprising polyoxyethylene group, water-soluble cellulose derivatives and the mixture thereof.

8. The pharmaceutical composition according to claim 7, wherein the weight ratio of the pharmacological active agent to the solubilizing carrier is 1:1-1:100.

9. The pharmaceutical composition according to claim 1, wherein the amount of pharmacological active agent is from 5 mg to 180 mg.

10. The pharmaceutical composition according to claim 9, wherein the amount of the pharmacological active agent is selected from the group consisting of 5 mg, 10 mg, 20 mg, 30 mg, 40 mg, 50 mg, 60 mg, 70 mg, 80 mg, 90 mg, 100 mg, 120 mg, 140 mg, 160 mg and 180 mg.

11. The pharmaceutical composition according to claim 9, wherein the composition is in a form selected from powders, granules, micro-pellets, tablets, capsules, dripping pills and lozenges.

12. A method for treating hypertension in a human being, comprising to administer orally the composition according to anyone of claims 9 to 11 comprising a therapeutically effective amount of 2-butyl-4-chloro-1-[2'-(1H-tetrazol-5-yl) 1,1'-biphenyl-methyl]imidazole-5-carboxylic acid, 1-[(isopropoxy)carbonyloxy]methyl ester in a human being in need thereof.

* * * * *